US 9,980,689 B2

(12) United States Patent
Gregerson et al.

(10) Patent No.: US 9,980,689 B2
(45) Date of Patent: *May 29, 2018

(54) DETECTOR SYSTEM FOR IMAGING DEVICE

(71) Applicant: Mobius Imaging LLC, Shirley, MA (US)

(72) Inventors: Eugene A. Gregerson, Bolton, MA (US); Paul Sebring, Townsend, MA (US); Russell Stanton, Lunenberg, MA (US); Michael Connor, Tyngsboro, MA (US); Michael Allen, Boxborough, MA (US); Scott Coppen, Amesbury, MA (US)

(73) Assignee: MOBIUS IMAGING, LLC, Shirley, MA (US)

( * ) Notice: Subject to any disclaimer, the term of this patent is extended or adjusted under 35 U.S.C. 154(b) by 37 days.

This patent is subject to a terminal disclaimer.

(21) Appl. No.: 14/847,184

(22) Filed: Sep. 8, 2015

(65) Prior Publication Data
US 2015/0374322 A1 Dec. 31, 2015

Related U.S. Application Data

(60) Continuation of application No. 13/915,442, filed on Jun. 11, 2013, now Pat. No. 9,125,613, which is a
(Continued)

(51) Int. Cl.
*A61B 6/00* (2006.01)
*A61B 6/03* (2006.01)

(52) U.S. Cl.
CPC ............. *A61B 6/4488* (2013.01); *A61B 6/03* (2013.01); *A61B 6/035* (2013.01); *A61B 6/4233* (2013.01)

(58) Field of Classification Search
CPC .......... A61B 6/00; A61B 6/03; A61B 6/4488; A61B 6/032; A61B 6/035
(Continued)

(56) References Cited

U.S. PATENT DOCUMENTS 5,912,943 A 6/1999 Deucher et al.
6,470,067 B1 10/2002 Harding
(Continued)

FOREIGN PATENT DOCUMENTS

JP 2011-154031 A 8/2011
JP 2011-220982 A 11/2011
KR 10-2012-0003900 A 1/2012

OTHER PUBLICATIONS

Supplementary European Search Report received from the European Patent Office for Application No. 13804539.8-1666/2858573, International Application No. PCT/US2013/045210 dated Feb. 2, 2016.
(Continued)

*Primary Examiner* — Jurie Yun
(74) *Attorney, Agent, or Firm* — The Marbury Law Group, PLLC

(57) ABSTRACT

A detector system for an imaging system includes an airflow cooling system. The detector system includes a detector chassis, a duct extending along the length of the chassis, and a manifold that couples the duct to the interior of the chassis. A vacuum source, such as a suction fan, is coupled to the duct and generates a vacuum force within the duct. The chassis includes a plurality of inlet openings, with an airflow path being defined through the interior of the chassis between the inlet openings and the manifold. The suction fan pulls cooling air through the inlet openings, through the chassis and manifold to the duct, and then expels the air through an exhaust opening. The airflow is directed into
(Continued)

thermal contact with detector elements and associated electronics in the detector chassis to provide cooling of these components.

14 Claims, 6 Drawing Sheets

Related U.S. Application Data continuation-in-part of application No. 14/810,529, filed on Jul. 28, 2015, now Pat. No. 9,576,378, which is a division of application No. 13/930,881, filed on Jun. 28, 2013, now Pat. No. 9,111,379.

(60) Provisional application No. 61/658,650, filed on Jun. 12, 2012, provisional application No. 61/665,482, filed on Jun. 28, 2012.

(58) Field of Classification Search
USPC .............................................. 378/4, 19, 189
See application file for complete search history.

(56) References Cited

U.S. PATENT DOCUMENTS

| | | | |
|---|---|---|---|
| 7,372,938 B2* | 5/2008 | Pohan | G01T 1/1648 378/189 |
| 7,586,095 B2* | 9/2009 | Lutz | A61B 6/035 250/370.09 |
| 2004/0131144 A1 | 7/2004 | Nishide et al. | |
| 2004/0247070 A1 | 12/2004 | Ali et al. | |
| 2005/0096523 A1 | 5/2005 | Vass et al. | |
| 2006/0126782 A1 | 6/2006 | Pohan et al. | |
| 2006/0261275 A1 | 11/2006 | Stearns et al. | |
| 2007/0041488 A1 | 2/2007 | Hoheisel et al. | |
| 2007/0165770 A1 | 7/2007 | Vogtmeier | |
| 2009/0010381 A1 | 1/2009 | Schlomka | |
| 2009/0129539 A1 | 5/2009 | Licato et al. | |
| 2009/0279660 A1 | 11/2009 | Takamatsu et al. | |
| 2011/0228910 A1 | 9/2011 | Gregerson et al. | |
| 2014/0003572 A1 | 1/2014 | Gregerson et al. | |
| 2014/0093039 A1 | 4/2014 | Yang et al. | |

OTHER PUBLICATIONS

EPO Communication pursuant to Rules 70(2) and 70a(2) EPC received from the European Patent Office for Application No. 13804539.8-166612858573, International Application No. PCT/US2013/045210 dated Feb. 23, 2016.

International Search Report and the Written Opinion of the International Searching Authority in International Application No. PCT/US2013/048631 dated Sep. 26, 2013.

International Preliminary Report on Patentability (Chapter 1 of the Patent Cooperation Treaty) in International Application No. PCT/U52013/048631 dated Jan. 8, 2015.

International Preliminary Report on Patentability (Chapter 1 of the Patent Cooperation Treaty) in International Application No. PCT/U52013/045210 dated Dec. 24, 2014.

* cited by examiner

DETECTOR SYSTEM FOR IMAGING DEVICE

RELATED APPLICATIONS

This application is a continuation of U.S. patent application Ser. No. 13/915,442 filed Jun. 11, 2013, which claims the benefit of priority to U.S. Provisional Application No. 61/658,650, filed Jun. 12, 2012, and is a continuation-in-part of U.S. patent application Ser. No. 14/810,529, filed Jul. 28, 2015, which is a divisional of U.S. patent application Ser. No. 13/930,881, filed Jun. 28, 2013, which claims the benefit of priority to U.S. Provisional Application No. 61/665,482, filed Jun. 28, 2012, the entire contents of all of which are incorporated herein by reference.

BACKGROUND

The present invention relates to a detector system, and in particular a detector system for a diagnostic imaging device, such as an x-ray CT scanning device.

A conventional x-ray CT scanning device is a large stationary device having a fixed bore, and is typically located in a dedicated x-ray room, such as in the radiology department of a hospital. In a typical device, an x-ray source and a detector system are mounted within a gantry defining an imaging bore, and rotate about an object being imaged. As the x-ray source and detector system rotate, the source projects a fan- or cone-shaped beam through the object being imaged, such as a patient, and the beam is attenuated by the object before impinging on the detector system. The detector system generally comprises an array of detector elements, where each element generates an electrical signal that represents the amount of attenuated beam radiation received at a particular detector location. The measurements from all detectors in the array together form a transmission profile that can be used to reconstruct images of the object, including three-dimensional tomographic images.

As the complexity and sophistication of diagnostic imaging systems continues to increase over time, the power output from the various components of the imaging system is also increasing. These imaging systems typically generate large amount of heat during normal operation. This can be problematic, since a number of components typically found in such imaging systems, including the detector system, are highly-temperature dependent. Thus, many imaging systems include cooling systems to help manage heat flow within the device. In commonly-owned U.S. application Ser. No. 13/025,573, filed Feb. 11, 2011, for example, an internal airflow cooling system is described for cooling the internal components of a mobile diagnostic imaging system.

Within the imaging system, the detector system presents unique issues in terms of heat management and control, since the detector is both highly heat-sensitive, due to the temperature dependence of the photo-sensitive detector elements, and is also a heat-generator, as a result of the complex system of electronics that is used to convert the output of the individual detector elements into (digital) electrical signals for further processing. To reduce space and minimize noise, these heat-generating electronics are typically close-coupled to the heat-sensitive detector elements within the detector system. The electronics can easily heat up the detector elements, resulting in a loss of image quality.

To deal with this issue, some imaging systems utilize cooling systems to maintain the heat-sensitive detector elements within normal operating temperatures. However, these cooling systems are generally large, complex and costly to implement. For example, U.S. Published Patent Application No. 2005/0117698 to Lacey et al. describes enclosing the detector electronics within a sealed refrigeration unit that includes a solid state heat pump (e.g., thermoelectric cooler) or heat pipe to cool the electronics.

While these large, complex and expensive cooling systems may be suitable for conventional diagnostic imaging systems, which are themselves very large, complicated and expensive devices, such cooling systems are not ideal for smaller and/or lower-cost devices, including mobile devices. There is therefore a need for a compact, low-cost and easily-implemented apparatus for managing temperature in the detector system of an imaging device.

SUMMARY

In embodiments, a detector system for an imaging device includes an airflow cooling system. The detector system may include a detector chassis forming a housing having a plurality of detector elements and associated electronics that extend along a length of the chassis. A duct may extend along the length of the chassis, and may be in fluid communication with the chassis housing via a manifold having a plurality of openings that extend along the length of the chassis. A vacuum source, such as a suction fan, may be coupled to the duct and generate a vacuum force within the duct. The chassis may include a plurality of inlet openings extending along the length of the chassis, with an airflow path being defined through the chassis housing between the plurality of inlet openings and the plurality of manifold openings. The suction fan may pull cooling air through the inlet openings into the detector chassis housing, through the manifold to the duct, and then expel the air from the detector system through an exhaust opening. The airflow may be directed into thermal contact with the detector elements and the associated electronics to provide cooling of these components.

In various embodiments, the suction fan and exhaust opening may be provided at one end of the chassis, with the exhaust opening directing the warmed exhaust air away from the chassis. In embodiments, the suction fan, exhaust opening, duct and manifold may be located proximate to one side surface of the chassis, and the inlet openings may be provided proximate to an opposite side surface of the chassis.

The detector chassis may be light-tight and substantially air-impermeable. In embodiments, the air inlet openings comprise two sets of openings, a set of outer openings and a set of inner openings, which are offset relative to one another. A filter material may fill the gap between the two sets of openings.

In one embodiment, a baffle may direct the airflow from the inlet openings into thermal contact with the detector elements and electronics. The chassis housing may include one or more internal passageways for directing the cooling airflow into thermal contact with the detector elements and the electronics. According to one embodiment, the temperature-sensitive components of the detector, such as the detector elements, may be positioned upstream of the heat-generating components, such as the electronics, in the cooling airflow path. The detector elements may be photodiodes, for example, and the electronics may include analog-to-digital converters.

In various embodiments, the detector system may be housed within a gantry of an imaging system, such as an x-ray CT imaging system. The detector system may be mounted to a rotor that rotates within the gantry.

Further embodiments include a method of controlling temperature within a detector system of an imaging system that includes directing a cooling fluid over a heat sensitive component of the detector system, directing the cooling fluid from the heat sensitive component over a heat generating component of the detector system, and directing the cooling fluid from the detector system.

Further embodiments include a detector system for an imaging system that includes means for directing a cooling fluid over a heat sensitive component of the detector system, means for directing the cooling fluid from the heat sensitive component over a heat generating component of the detector system, and means for directing the cooling fluid from the detector system.

Further embodiments include an x-ray CT imaging system that includes an x-ray source and a detector system housed within an imaging gantry for obtaining images of an object positioned within an imaging bore of the gantry, wherein the detector system comprises a detector chassis forming a housing having a plurality of detector elements and associated electronics located along a length of the chassis, a duct extending along the length of the chassis, a manifold having a plurality of openings extending along the length of the chassis, the manifold providing fluid communication between the duct and the chassis housing, a vacuum source coupled to the duct that generates a vacuum force within the duct, a plurality of inlet openings extending along the length of the chassis housing, an airflow path being defined through the chassis housing between the plurality of inlet openings and the plurality of manifold openings, the detector elements and associated electronics being located along the airflow path, and an exhaust opening coupled to the vacuum source for removing air from the detector system.

Further embodiments include methods of imaging an object, such as a human or animal patient, using an imaging detector system having an airflow cooling system.

In various embodiments, an airflow cooling system may provide a compact, low-cost and easily-implemented solution for controlling temperature within an imaging detector system.

BRIEF DESCRIPTION OF THE DRAWINGS

Other features and advantages of the present invention will be apparent from the following detailed description of the invention, taken in conjunction with the accompanying drawings of which.

DETAILED DESCRIPTION

This application is related to U.S. application Ser. No. 12/576,681, filed Oct. 9, 2009, now U.S. Pat. No. 8,118,488, U.S. application Ser. No. 13/025,566, filed Feb. 11, 2011, U.S. application Ser. No. 13/025,573, filed Feb. 11, 2011, and U.S. application Ser. No. 13/441,555, filed Apr. 6, 2012. The entire contents of all of these applications are hereby incorporated by reference for all purposes.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

Figure 1A:
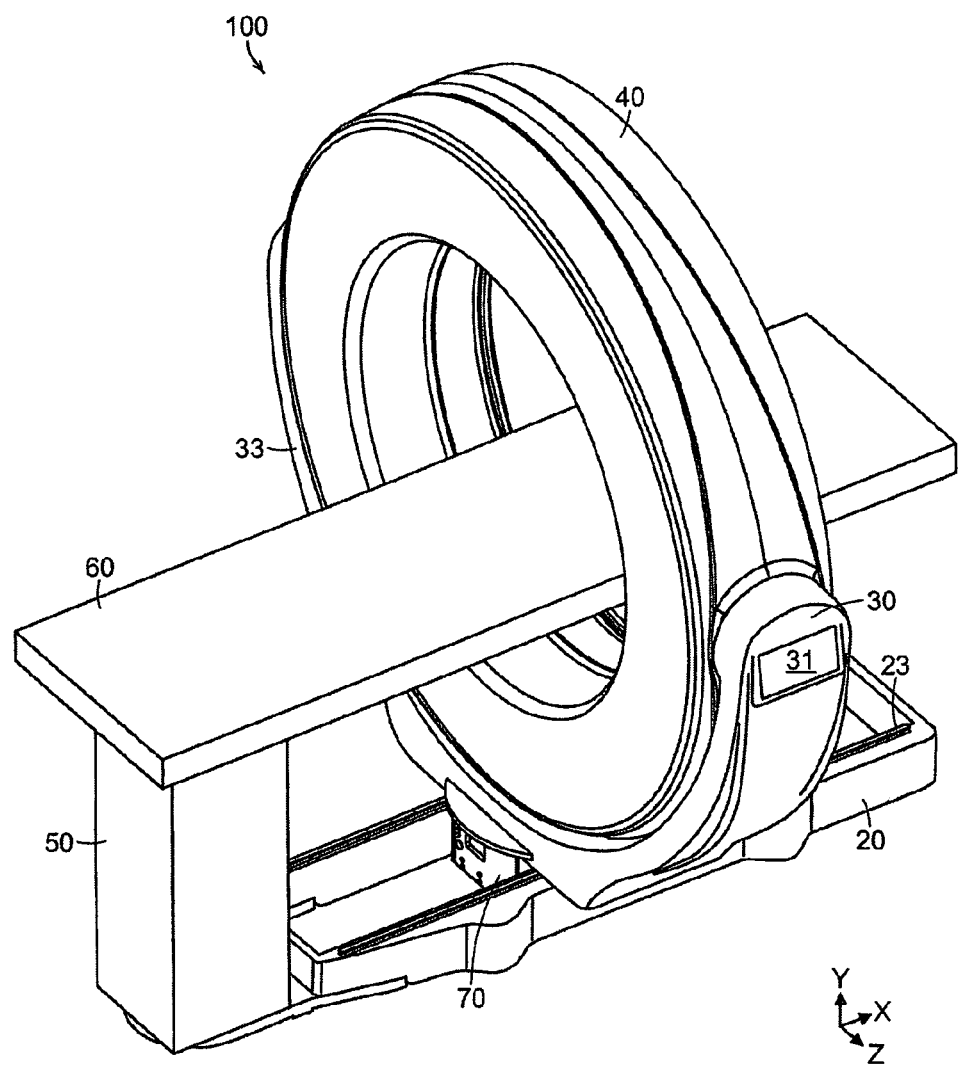
FIG. 1A is a perspective view of an X-ray CT imaging system in accordance with one embodiment of the invention.
Figure 1B:
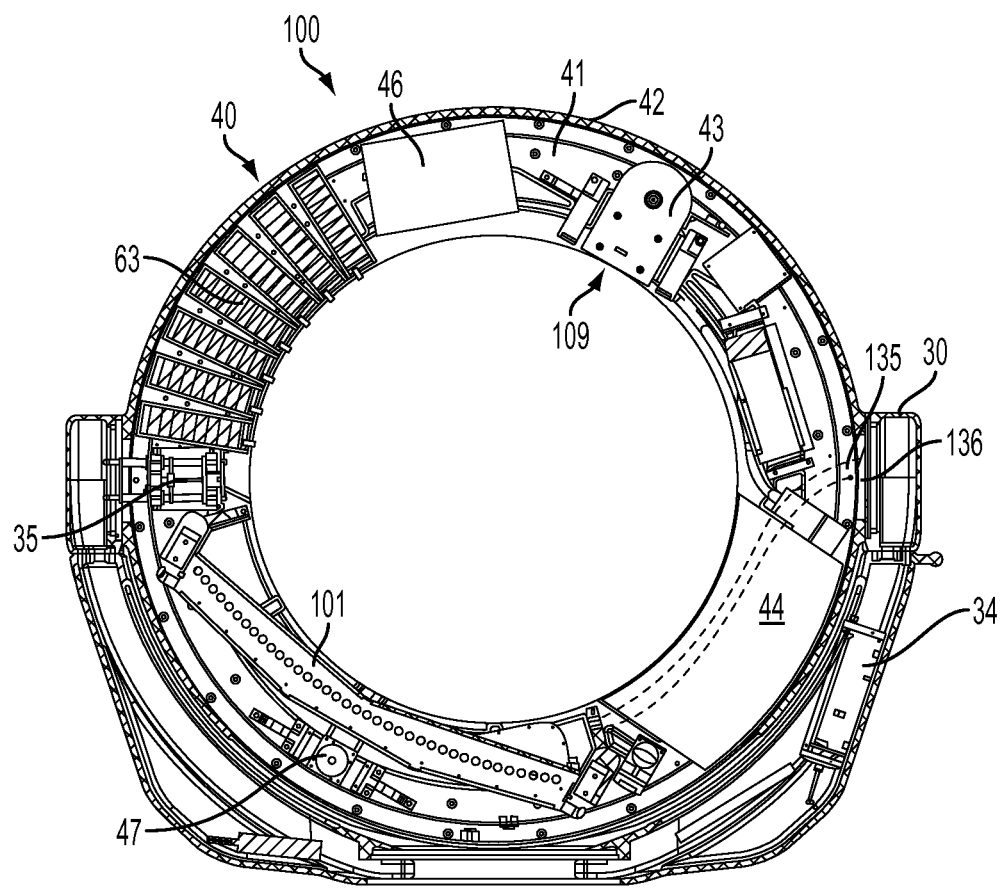
FIG. 1B is a cross-sectional view of an X-ray CT imaging system with an detector system of the invention.
Figure 2:
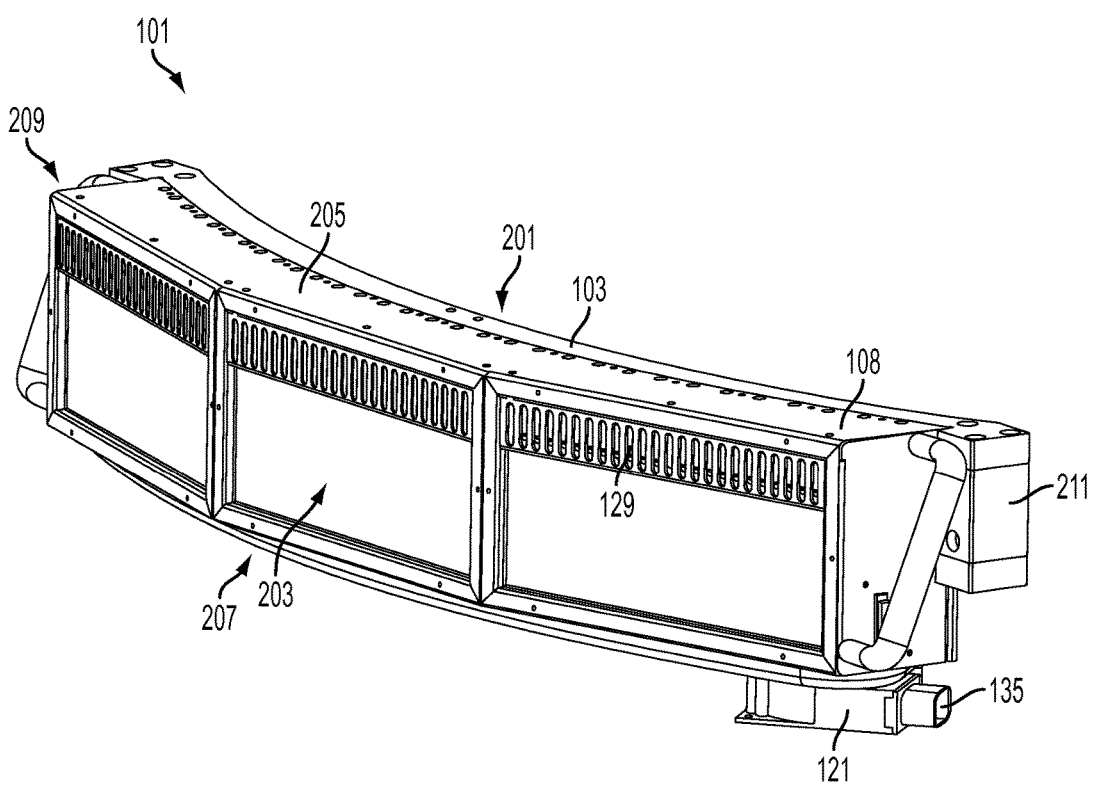
FIG. 2 is a rear perspective view of a detector system according to one embodiment.

The present invention relates to a detector system, and in particular a detector system for a diagnostic imaging device, such as an x-ray CT scanning device. An exemplary embodiment of an imaging device 100 is illustrated in FIGS. 1A and 1B. Referring to FIG. 1A, the imaging device 100 includes a mobile base 20, a gimbal 30, a gantry 40, and a pedestal 50. The system 100 includes image collection components, such as a rotatable x-ray source and detector array or stationary magnetic resonance imaging components, that are housed within the gantry 40. The system 100 is configured to collect imaging data, such as, for example x-ray computed tomography (CT) or magnetic resonance imaging (MRI) data, from an object located within the bore of the gantry 40, in any manner known in the medical imaging field. The pedestal 50 is adapted to support a tabletop support 60 that can be attached to the pedestal 50 in a cantilevered manner and extend out into the bore of the gantry 40 to support a patient or other object being imaged.

The gimbal 30 is a generally C-shaped support that is mounted to the top surface of base 20 and includes a pair of arms 31, 33 extending up from the base. The arms 31, 33 are connected to opposite sides of gantry 40 so that the gantry is suspended above base 20 and gimbal 30. In one embodiment, the gimbal 30 and gantry 40 may rotate together about a first axis generally normal to the top surface of the base 20, and the gantry 40 may tilt with respect to the gimbal arms 31, 33.

In certain embodiments, the gimbal 30 and gantry 40 may translate with respect to the base 20 to provide an imaging scan. The gimbal 30 may include bearing surfaces that travel on rails 23, as shown in FIG. 1A, to provide the translation motion of the gimbal 30 and gantry 20. A scan drive mechanism may drive the translation of the gantry and gimbal relative to the base, and a main drive mechanism can drive the entire system in a transport mode. In the embodiment of FIG. 1A, both of these functions are combined in a drive system 70 that is located beneath the gimbal 30.

FIG. 1B is a cross-sectional view of the gantry 40 and gimbal 30 that illustrates a number of components of the imaging system 100, including an x-ray source 43, high-voltage generator 44, detector system 101, battery system 63, computer 46, rotor drive mechanism 47, docking system 35 and charging system 34. A number of these components, including the x-ray source 43, high-voltage generator 44, detector 101, battery system 63, computer 46 and rotor drive mechanism 47, are mounted on a rotor 41. The rotor 41 and the components mounted thereto, rotate within a housing defined by an outer shell 42 of the gantry 40.

During an imaging scan, the rotor 41 rotates within the interior of the gantry, while the imaging components such as the x-ray source 43 and detector system 101 operate to obtain imaging data for an object positioned within the bore of the gantry, as is known, for example, in conventional X-ray CT scanners. The rotor drive mechanism 47 drives the rotation of the rotor 41 around the interior of the gantry 40. The rotor drive mechanism 47 may be controlled by a system controller that controls the rotation and precise angular position of the rotor 41 with respect to the gantry 40, preferably using position feedback data, such as from a position encoder device.

Various details of embodiments of an imaging system can be found in the above-referenced U.S. application Ser. Nos. 12/576,681, 13/025,566, 13/025,573, and 13/441,555, which have been incorporated herein by reference. It will be understood that these embodiments are provided as illustrative, non-limiting examples of imaging systems suitable for use with the present detector system, and that the present detector system is suitable for use in any number of other imaging systems of various types, now known or later developed.

The detector system in accordance with one embodiment of the invention is shown in FIG. 2-5. The detector system 101 is shown in a rear perspective view in FIG. 2 and a front perspective, cross-sectional view in FIG. 3. The detector system 101 includes a detector chassis 103 (e.g., detector carriage) having a depth defined by front 201 and rear 203 surfaces, a width defined by a first side surface 205 and a second side surface 207, and a length between a first end 209 and a second end 211. In one embodiment, the detector chassis 103 has a width of 7¾ inches, a depth of between about 4-5 inches and a length of about 1 meter or more, such as about 43 inches.

Figure 3:
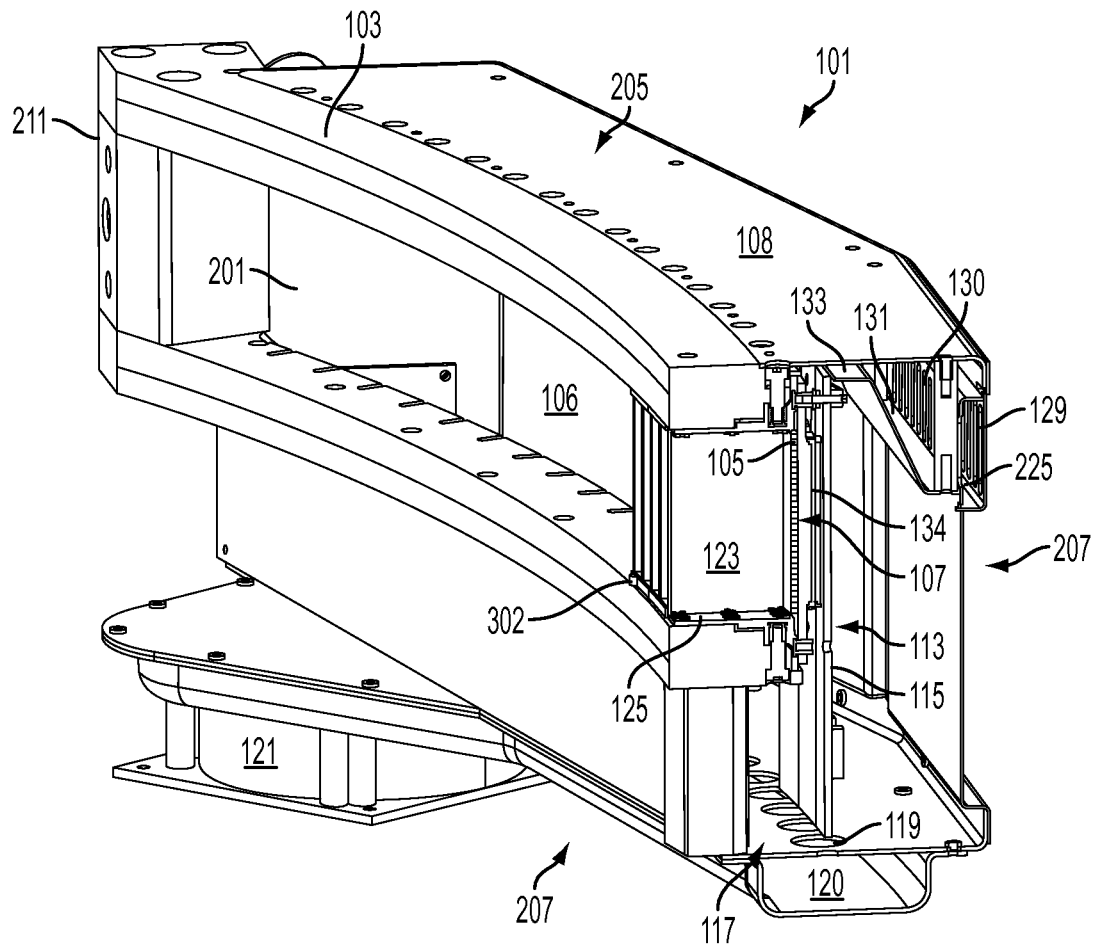
FIG. 3 is a front perspective view of the detector system, showing a cross-section of the system.

The detector chassis 103 may be a rigid frame, which may be formed of a metal material, such as aluminum, and which may be formed by a suitable machining technique. The detector chassis 103 may support a plurality of detector elements and associated electronics. In one embodiment, the detector chassis 103 is mounted to the rotor 41, opposite the x-ray source 43, as is shown in FIG. 1B. As seen in FIG. 3, the front surface 201 of the chassis 103 includes a cavity 106 extending along the length of the chassis 103. A plurality of x-ray-sensitive detector elements 105 are provided in the interior of the cavity 106, facing out from the cavity and in the direction of the x-ray source 43 (FIG. 1B). The rear 203, side 205, 207 and end 209, 211 surfaces of the detector system 101 together may form a protective shroud 108 around the cavity 106 and the detector elements 105 positioned therein. The shroud 108 is preferably air- and light-tight, meaning it prevents unwanted air and light from entering into the cavity 106 and contaminating the sensitive components housed within the detector system 101. The interior surfaces of the shroud 108 can be lined with a light-tight material.

In various embodiments, the detector elements 105 may be located on a plurality of detector modules 107. Each individual detector element 105, which may be for example, a cadmium tungstate ($CdWO_4$) material coupled to a photodiode, represents a pixel on a multi-element detector module. The modules 107 may be a two-dimensional (2D) element array, with for example 512 pixels per module.

The detector system 101 may include one or more detector modules 107 mounted within the detector chassis 103. The module(s) 107 may be arranged along the length of the chassis 103 to form or approximate a semicircular arc, with the arc center coinciding with the focal spot 109 of the x-ray source 43 (see FIG. 1B). In one embodiment, the detector system 101 includes thirty-one two-dimensional detector modules 107 positioned within the cavity 106 along the length of the chassis 103, and angled relative to each other to approximate a semicircular arc centered on the focal spot of the x-ray source. Each module 107 may be positioned such that the module detector surface is normal to a ray extending from the x-ray focal spot 109 to the center pixel of the module 107.

The system may further include a collimator located within the cavity 106 in front of the array of detector elements 105. In various embodiments, the collimator may comprise a plurality of anti-scatter plates 123, which are thin plates made from an x-ray absorbent material, such as tungsten or lead. Each of the plates 123 may be arranged generally perpendicular to the adjacent detector module 107 and the set of plates 123 may be focused at the x-ray focal spot 109 (see FIG. 1B). In a preferred embodiment, each plate 123 is provided between adjacent columns of elements (pixels) of the module 107 so as to inhibit scattered x-rays, traveling at an oblique angle, from impinging on the detector elements. The anti-scatter plates 123 may be provided so that the detector elements primarily measure the intensity of x-rays that travel along a straight-line path from the x-ray source to the detector. Although the anti-scatter plates in this embodiment are provided between each column of detector elements, it will be understood that other configurations can be utilized, including arranging anti-scatter plates between rows of detector elements, and/or between columns and rows in an anti-scatter "grid" configuration.

In the embodiment of FIG. 3, the anti-scatter plates 123 may be held in place by support elements 125 that are mounted to the detector chassis (carriage) 103. The support elements 125 may comprise injected-molded plastic components having alignment features that allow the plates 123 to simply slide into place in the support element 125 and ensure that the plates are secured in proper alignment within the desired tolerances, with respect to both the x-ray source and the detector array elements. Similarly, the detector modules 107 may be inserted into slots or other alignment features that secure them into proper orientation with respect to each other and to the x-ray focal spot.

Figure 4:
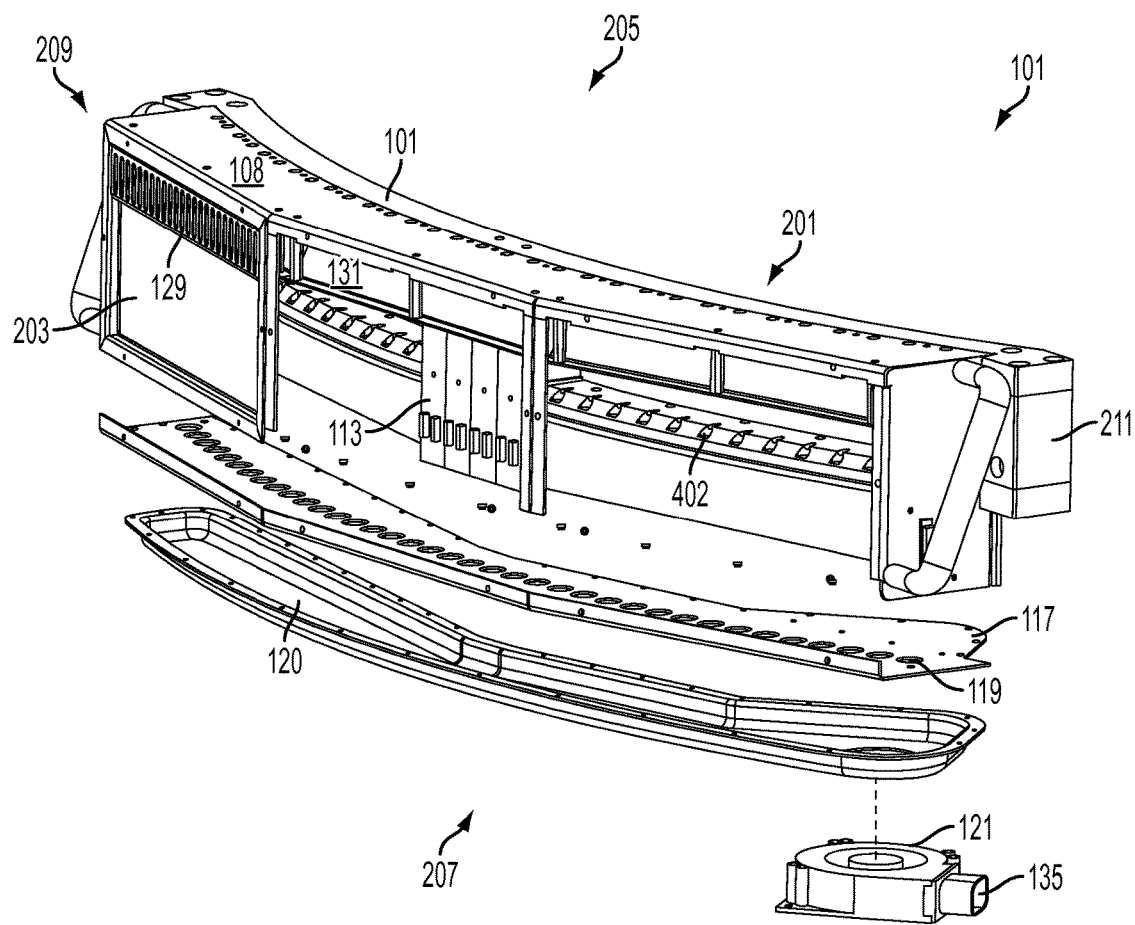
FIG. 4 is an exploded rear view of the detector system illustrating components of a cooling system, according to one embodiment.

The support elements 125 and/or the detector chassis 103 may include alignment features that are configured to position the support elements 125 in a desired position within the detector system 101. For example, as shown in FIG. 4, the detector chassis 103 may include openings 402 that may be configured to receive mating protuberances on the support elements 125. Alternatively or in addition, the detector chassis 103 may include protuberances 302 that may fix the position of the support elements 125 on the detector chassis 103, as shown in FIG. 3.

Each detector module 107 may include associated electronics 113, which in one embodiment are provided on one or more electronic circuit boards mounted behind the respective detector modules 107 in the detector chassis 103. In operation, according to various embodiments, each of the detector elements 105 produces an analog electronic signal in response to x-rays received from the x-ray source 43, and these analog signals are sent to the electronics 113 for digitization and further processing. In one embodiment, each detector module 107 has one or more associated analog-to-digital (A/D) converters 115 for converting the analog electrical signals generated by each detector element 105 into digital signals for additional processing.

In accordance with one aspect of the invention, the detector system 101 includes a cooling system for maintaining the temperature of the detector elements 105 within pre-determined temperature parameters. It is known that the performance of many detector elements, such as photo-diodes, is temperature dependent. Increases in detector temperature can induce increases in dark current, for example, which can reduce the quality of the images obtained by the imaging system. This is problematic, since many of the components of the imaging system, such as the x-ray tube and high-voltage generator, generate large quantities of heat during operation, which can heat up the detector system and the temperature-sensitive detector elements mounted therein. This problem can be managed, at least in part, by the use of a gantry cooling system, such as the air-flow cooling system described in U.S. application Ser. No. 13/025,573, which has been incorporated herein by reference.

Even more problematic, however, is that there are a number of heat-generating components located within the detector system itself, including, for example, the electronics 113 components which are closely-coupled to the detector elements 105 inside the detector chassis 103. The A/D converters, in particular, are known to generate a relatively large amount of heat (e.g. 1-2 kW) that can cause an undesirable temperature rise in the detector elements.

Accordingly, the detector system 101 in one embodiment comprises a cooling system that is designed to control the temperature of the temperature-sensitive detector elements. The cooling system in this embodiment comprises an airflow cooling system that directs cooling air from the gantry housing into and through the detector chassis 103, where the air thermally contacts the heat-sensitive detector elements and heat-generating electronics components, and then out of the detector system 101 through an exhaust opening 135. The cooling air flow acts as a heat transfer medium, picking up heat from the detector elements and electronics, and carrying this heat out of the detector system. In this manner, the cooling system is able to control the temperature within the detector system, and in particular, maintains the highly temperature-sensitive detector elements within desired operating temperatures.

Several components of an embodiment of the detector cooling system are best illustrated in the exploded view of FIG. 4. A suction fan (blower) 121, with an exhaust opening 135, is located on the second side surface 207 of the detector chassis 103. In a preferred embodiment, the suction fan 121 is located proximate the end surface 111 of the chassis 103, with the exhaust opening 135 directed away from the chassis 103. The suction fan 121 is in fluid communication with a duct 120 that extends along the entire second side surface 207 of the chassis 103. A manifold 117 having a plurality of holes 119 also extends along the second side surface 107, and connects the duct 120 to the interior cavity of the chassis 103.

During operation of the detector system 101, the suction fan 121 may produce a negative pressure within the duct 120, causing air from the interior cavity 106 of the chassis 103 to be sucked through the holes 119 of the manifold 117 into the duct and then blown out of the detector system 101 through the exhaust opening 135. As the heated air from the interior of the chassis is evacuated, cooler air is pulled into the chassis through air inlet openings 129, 130 provided in the rear surface 203 of the chassis 103.

In one preferred embodiment, the inlet openings 129, 130 are located proximate the first side surface 205 of the chassis 103, while the manifold 117, duct 120 and suction fan 121 are located proximate the second side surface 107 of the chassis 103. In this way, the airflow path of the cooling air encompasses substantially the entire width of the chassis 103 between the first and second side surfaces, 106 and 107, respectively. Also, locating the inlet openings 129, 130 on the opposite side of the chassis 103 from the exhaust opening 135 helps minimize the chance that the relatively hotter air exiting from the exhaust opening 135 could enter the inlet openings 129, 130 and recirculate through the chassis 103.

In some embodiments, the exhaust opening 135 can direct the exhaust air away from the detector system 101 and out of the gantry 40 entirely, such as through one or more vents or openings in the outer shell 42 of the gantry 40. FIG. 1B schematically illustrates one embodiment, for example, in which the exhaust opening 135 comprises an extended duct or pipe that directs the exhaust air away from the detector system 101 and towards other heat-generating components of the imaging system, such as the x-ray tube 43 and high-voltage generator 44. The imaging system may be configured such that between imaging scans, when the rotor 41 is not rotating, the rotor 41 rotates to a "park" position where the exhaust opening 135 is positioned adjacent to an opening 136 in the gantry shell 42 so that the heated air can be removed from the gantry 40. The detector cooling system of the invention may operate in conjunction with a gantry cooling system of the type described in U.S. application Ser. No. 13/025,573, which has been incorporated herein by reference.

In one embodiment, the inlet openings 129, 130 comprise two sets of slots, a set of outer slots 129 and a set of inner slots 130, as best illustrated in FIG. 3. The two sets of slots 129, 130 may be offset relative to each other along the length of the chassis, which helps maintain the light-impermeability of the protective shroud 108. In a preferred embodiment, the gap 225 between the outer and inner slots may be filled with a suitable filter material (not shown) to prevent particles and other contaminants from entering the interior of the chassis. The filter material may be light-tight.

A baffle 131 may be located adjacent the inner set of slots 130. The baffle 131 directs the inlet airflow to a small gap 133 between the baffle 131 and the inner side wall of the chassis 103. From there, the airflow is directed through one or more passage(s) 134 extending along the width of the chassis 103. Here, the cooling airflow preferably comes into direct thermal contact with the detector modules 107 and the circuit boards containing the A/D converters 115 and other electronic components 113. The airflow, now heated by heat transfer from the detector elements and associated electronics, exits though the holes 119 into the duct 120, and is then forced by suction fan 121 out through exhaust opening 135. This airflow path is schematically illustrated by a dotted line in the cross-sectional elevation view of FIG. 5.

Figure 5:
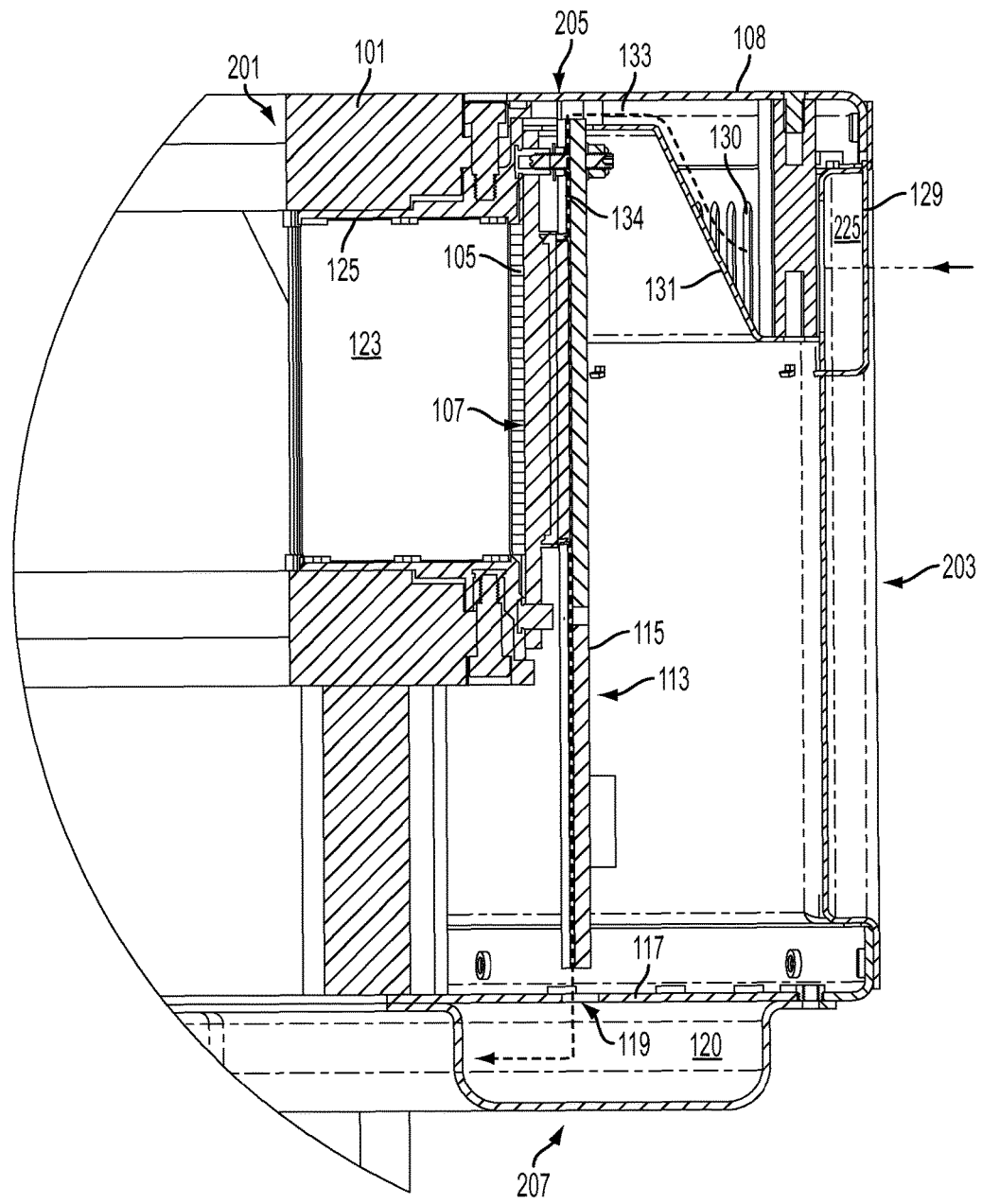
FIG. 5 is a cross-section view of the detector system illustrating a flow path for cooling air.

According to one preferred embodiment, as shown in FIG. 5, the detector elements 105 are located upstream of the heat-generating electronic components 113, 115 along the airflow path. The cooling air first flows over the detector elements 105, removing heat from the detector elements 105, and then flows over the electronics 113, 115, where the air picks up additional heat from the relatively hotter electronics components. The A/D converters 115, in particular, which generate significant heat, are preferably located closer to the second side surface 207 than the detector elements 105, which are closer to the first side surface 205, where the air-flow is coolest. This configuration provides efficient cooling of the heat-sensitive detector elements.

The inlet openings 129, 130 and manifold holes 119 may extend generally along the entire length of the chassis 103 to provide uniform cooling of the detector elements over the length of the detector array. In some embodiments, the holes 119 in the manifold 117 may have variable size and/or spacing between holes to promote uniform air-flow and cooling over the length of the detector. This may be beneficial, for example, to compensate for variations in the suction force along the length of the duct 120. The suction force will generally be greatest at locations near the suction fan 121, and can decrease as the distance from the fan 121 becomes great. As an alternative or in addition to varying the size and/or spacing of the manifold holes 119, the inlet openings 129, 130 may have varying size and/or spacing along the length of the chassis to promote uniform air-flow.

The foregoing method descriptions are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not necessarily intended to limit the order of the steps; these words may be used to guide the reader through the description of the methods. Further, any reference to claim elements in the singular, for example, using the articles "a," "an" or "the" is not to be construed as limiting the element to the singular.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

What is claimed is:

1. A method of controlling temperature within a detector system of an imaging system, comprising:
   directing a cooling fluid directly over a heat sensitive component of the detector system;
   directing the cooling fluid from the heat sensitive component directly over a heat generating component of the detector system; and
   directing the cooling fluid from the detector system.

2. The method of claim 1, wherein the cooling fluid comprises air.

3. The method of claim 1, wherein the heat sensitive component and the heat generating component of the detector system are located in a housing, and wherein directing the cooling fluid over the heat sensitive component and the heat generating component comprises operating a vacuum source in fluid communication with the housing.

4. The method of claim 3, wherein the vacuum source comprises a suction fan.

5. The method of claim 3, wherein directing the cooling fluid from the detector system comprises directing the cooling fluid through an exhaust opening coupled to the vacuum source.

6. The method of claim 3, wherein the detector system further comprises at least one opening in fluid communication with the housing, wherein directing the cooling fluid further comprises directing the cooling fluid through the at least one opening and over the heat sensitive and heat generating components.

7. The method of claim 6, further comprising directing the cooling fluid from the housing through a manifold coupled to a duct, and directing the cooling fluid from the duct out of the detector system.

8. The method of claim 1, wherein the heat sensitive component comprises a photodiode.

9. The method of claim 8, wherein the heat generating component comprises an analog-to-digital converter.

10. The method of claim 1, wherein the detector system is housed within a gantry of the imaging system.

11. The method of claim 10, further comprising rotating the detector system on a rotor within the gantry of the imaging system.

12. The method of claim 10, wherein the imaging system comprises an x-ray CT imaging system.

13. The method of claim 10, further comprising directing the cooling fluid out of the gantry.

14. A detector system for an imaging system, comprising:
    means for directing a cooling fluid directly over a heat sensitive component of the detector system;
    means for directing the cooling fluid from the heat sensitive component directly over a heat generating component of the detector system; and
    means for directing the cooling fluid from the detector system.

* * * * *